United States Patent [19]
Koyama et al.

[11] Patent Number: 6,123,934
[45] Date of Patent: Sep. 26, 2000

[54] HAIR COSMETIC COMPOSITION

[75] Inventors: Takashi Koyama, Chiba; Kazuyo Watanabe, Wakayama; Hiroshi Nojiri, Utsunomiya; Sachio Naito, Tsukuba; Michitaka Sawada, Wakayama; Genji Imokawa, Utsunomiya; Hidehisa Takahashi; Toshiki Kobayashi, both of Yokkaichi, all of Japan

[73] Assignees: Kao Corporation, Tokyo; Taiyo Kagaku Co., Ltd., Yokkaichi, both of Japan

[21] Appl. No.: 08/879,812

[22] Filed: Jun. 20, 1997

Related U.S. Application Data

[63] Continuation of application No. 08/407,959, Mar. 22, 1995, abandoned.

[30] Foreign Application Priority Data

Mar. 24, 1994 [JP] Japan .................................. 6-053363

[51] Int. Cl.$^7$ ................ A61K 7/07; A61K 7/00
[52] U.S. Cl. ................. 424/70.11; 424/70.1; 424/70.17; 424/130.1
[58] Field of Search ............... 424/70.1, 70.11, 424/70.16, 70.17, 70.12, 130.1

[56] References Cited

U.S. PATENT DOCUMENTS

| | | | |
|---|---|---|---|
| 3,987,161 | 10/1976 | Widder | 424/70 |
| 4,798,721 | 1/1989 | Yahagi et al. | 424/70 |
| 5,120,532 | 6/1992 | Wells | 424/70.11 |

FOREIGN PATENT DOCUMENTS

| | | |
|---|---|---|
| 0 214 626 | 3/1987 | European Pat. Off. . |
| 0 542 309 | 5/1993 | European Pat. Off. . |
| 0 570 583 | 11/1993 | European Pat. Off. . |

OTHER PUBLICATIONS

Tizard, An Introduction to Veterinary Immunology, (1977) p. 168.
Database WPI, Derwent Publications, AN–93–005491, JP–A–04 334312, Nov. 20, 1992.
Japanese Abstract (JP05139935–A) Jun. 8, 1993.
Japanese Abstract (JP 5139935) Jun. 8, 1993.
Japanese Abstract (JP 57163392) Oct. 7, 1982.
Japanese Abstract (JP 57085308) May 28, 1982.
Japanese Abstract (JP 3145500) Jun. 20, 1991.
Japanese Abstract (JP 1038098).

*Primary Examiner*—Sally Gardner Lane
*Attorney, Agent, or Firm*—Oblon, Spivak, McClelland, Maier & Neustadt, P.C.

[57] ABSTRACT

The present invention provides a hair cosmetic composition containing an antibody (a) to hair or a hair extract obtained from egg yolk of poultry immunized with the hair or hair extract, and a polymer emulsion (b). The hair cosmetic composition of the invention can provide excellent properties including softness, moistened feel, and smoothness. In addition, since it is adsorbed only onto a specified part of the hair, stickiness or greasiness of the hair can be prevented. The composition also prevents occurrence of split hairs, and even repair the split hairs. These effects are not lost by repeated ordinary shampooings.

15 Claims, No Drawings

HAIR COSMETIC COMPOSITION

This application is a Continuation of application Ser. No. 08/407,959, filed on Mar. 22, 1995, now abandoned.

BACKGROUND OF THE INVENTION

1. Field of the Invention

The present invention relates to a hair cosmetic composition which imparts an excellent tactile feel to the hair and which suppresses or reverses damage to the hair.

2. Description of the Related Art

Recently, with the indivisualty of fashion, long hair has become increasingly popular. In addition, beauty treatments such as partial permanents have brought variations to hair-dos of long hair. On the other hand, hair damage such as split hairs and broken hairs have increased. Such hair damage is considered to be caused by chemical treatments such as permanents which denature the keratinous protein of the hair to weaken the inside structure of the hair fibers and render the hair fibers vulnerable to mechanical forces applied when the hair is dried with a drier or is brushed.

In order to prevent hair from being damaged, it has been attempted to avoid degradation of the protein structure caused by chemical treatments by incorporating collagen, keratin proteins, and similar substances into hair care compositions to form a protective film on the surface of hair fibers, to impart moisture-retainability to hair fibers, or to enhance the elasticity of hair fibers (see, for example, Japanese Patent Application Laid-open (kokai) No. 61-280,413). Alternatively, it is also known to incorporate oily ingredients such as higher alcohols, ester oils, liquid paraffins, or silicone oils into hair rinses, treatments, brushing agents, setting agents, etc. in an attempt to reduce friction on the surface of hair fibers. However, hair care compositions containing collagen, keratinous proteins and the like do not sufficiently prevent damage to the hair. Furthermore, products containing oily ingredients are not sufficiently effective in reducing friction, and if the amount of incorporation of the oily ingredients is increased with an aim to improve their effect, the composition causes an unpleasant stickiness or greasiness.

Hair care compositions which contain polymer emulsions as a hair conditioning agent are known to solve the above problems (Japanese Patent Application Laid-open (kokai) No. 62-63,508). Polymer emulsions ensure adsorption of fine particles of the polymer onto hair fibers. Therefore, larger amounts of the polymer can be adsorbed compared to a low molecular weight hair conditioning agents which are adsorbed onto hair fibers as molecules, resulting in greater effectiveness. Polymer emulsions, however, have the drawback that they do not have selectivity when adsorbed onto hair fibers. They are adsorbed not only by damaged hair (hair fibers from which cuticles are scaled off), but also by healthy hair. If a polymer emulsion is adsorbed by healthy hair, the smooth tactile feel which the hair inherently possesses and natural texture of the hair are lost. This problem is more prominent when polymer emulsions are used than when low molecular weight hair conditioning agents are used, because polymer emulsions are adsorbed in larger amounts.

As described above, conventional hair cosmetic compositions do not necessarily provide satisfactory effects. Especially, most of them have insufficient damage prevention or restorative effects.

SUMMARY OF THE INVENTION

Accordingly, an object of the present invention is to provide a hair cosmetic composition which suppresses or reverses damage to the hair while maintaining the natural qualities of undamaged healthy hair fibers, and which imparts elasticity, softness, and smoothness to the entire hair fibers while reducing an oily sensation, by selectively permitting particles in a polymer emulsion to be adsorbed by the damaged part of hair fibers.

In order to achieve the above object, the present inventors carried out extensive studies and found that when a mixture of an antibody against the hair obtained from egg yolk of poultry and a certain polymer emulsion is applied to the hair, these two components are not independently bound to or adsorbed by the hair fibers, but the antibody is adsorbed by the particles of the polymer emulsion, and surprisingly, the polymer emulsion is selectively adsorbed by a specified portion of the hair fibers due to the specificity of the antibody to suppress damage to the hair fibers or repair the damage while maintaining the natural tactile feel of the hair. The present invention was accomplished based on this finding.

A hair cosmetic composition according to the present invention comprises (a) an antibody to hair or a hair extract obtained from an egg yolk of a hen immunized with the hair or hair extract and (b) a polymer emulsion.

DESCRIPTION OF PREFERRED EMBODIMENTS

The antibody (a) which is used in the present invention is obtained from the yolk of an egg of a hen which has been immunized with hair or a hair extract (Japanese Patent Application Laid-open (kokai) No. 5-1,399,335).

Examples of the hair or hair extract include a powdery material obtained by powderizing a whole fiber or structural tissues (cuticle, cortex, medulla, etc.) of healthy hair or damaged hair which was damaged by a permanent treatment, etc. to a size of 100 $\mu$m or less, or a keratin protein or a hydrolysate thereof extracted from the hair. In order to obtain an antibody having specificity to damaged hair, hair powder or a keratin protein which has undergone a chemical treatment such as permanent treatment can also be used.

The method of powderizing the whole hair or structural tissue of the hair is not particularly limited. For example, the hair which has been swollen with water may be frozen and crushed as described in Japanese Patent Application Laid-open (kokai) No. 57-163,392 (from line 4 of the lower left column in page 2 to line 12 of the upper left column in page 4). Alternatively, the hair may be swollen by treatment with a protein denaturing agent such as lithium bromide, urea, and guanidine hydrochloride, and then frozen and crushed with a crusher such as a mortar or a sand mill at the temperature of liquid nitrogen. Cortex powder can be obtained by removing cuticles from the hair by a Vantean treatment described in "Proceeding of the 7th International Wool Textile Research Conference", vol. 4 (1985), p.p. 322–331, and then crushing the residue by the method for crushing whole hair described above. Cuticle powder can be obtained by shaking pieces of hair which has been cut to a size of not more than 1 cm in sterilized water along with beads made of teflon to mechanically exfoliate cuticles, collecting the exfoliated cuticles by centrifugal separation or filtration, and then freeze-drying the cuticles.

Extraction of a keratin protein from hair fibers may be carried out using a protein denaturing agent such as urea, guanidine hydrochloride, or sodium dodecyl sulfate in the presence of a reducing agent such as mercaptoethanol, dithiothreitol, tributylphosphine, thioglycol acid, etc. The resulting keratin protein may further be treated by blocking its thiol group with acetic iodide, acetamide iodide, N-ethylmaleimide, and the like, or the keratin protein may be fractionated by chromatography (as described in "Biochemistry and Physiology of the Skin", edited by Lowell A. Goldsmith, Vol. 1 (1983), page 476, Oxford University Press, or "The Japanese Journal of Dermatology", Vol. 98 (1988), pp. 619–620). A hydrolysate of the keratin protein can be obtained by hydrolyzing the keratin protein with acids, alkalis, or enzymes which are described in Japanese Patent Application Laid-open (kokai) No. 57-85,308 (from line 7 of the upper left column of page 3 to line 12 of the upper left column of page 4).

Immunization of poultry may be performed by subcutaneously, intraperitoneally, or intramuscularly injecting an antigen to various species of poultry. Alternatively, the poultry may be forcibly given the antigen orally. An example of a species of poultry which can be used is a chicken. The amount of the antigen to be administered for immunization is determined so as to achieve a desired antibody titer within the range which does not adversely affect the poultry to be immunized. If necessary, a complete Freund adjuvant (FCA) or an incomplete Freund adjuvant (FIA) may be used in combination.

Next, methods for collecting an antibody fraction (immunoglobulin) from the yolk will be described in detail.

In order to collect an immunoglobulin from the yolk, the methods described in "Proceeding of the Society for Experimental Biology and Medicine", Vol. 126 (1967), page 312; "Immunology Communications", Vol. 9 (1980), page 495; and Japanese Patent Application Laid-open (kokai) No. 3-145,500 (see from line 2 of the upper right column to line 12 of the lower left column in page 3) may be applied. In one example of such methods, the yolk separated from an egg is combined with an equivalent amount of phosphate-buffered saline (PBS), after which twice the amount of a fat-soluble solvent such as chloroform and isopropyl alcohol is added to remove fractions of lipids. From the resulting aqueous phase, a roughly purified immunoglobulin is obtained by an ammonium sulfate fractionation technique (roughly purified antibody). If necessary, a further fractionation will be carried out using ion exchanging or affinity exchanging means. Finally, gel filtration fractionation will be performed (highly purified antibody). Since immunoglobulin may be denatured by the above methods, it is preferable to use the method described in Japanese Patent Application Laid-open (kokai) No. 64-38,098, from lines 8 to 15 of the lower left column at page 5 (see also Preparation Example 2 described herebelow).

The thus obtained antibody (a) may be incorporated into hair cosmetic compositions in a liquid state. However, it is more preferred that the antibody (a) be condensed by distillation under reduced pressure or be freeze-dried before being incorporated into the compositions.

The amount of the antibody (a) which is incorporated into hair cosmetic compositions differs depending on whether the antibody is a highly purified one or roughly purified one. Generally speaking, the amount is preferably from 0.001 to 50% by weight on a freeze-dried basis. In the case where a highly purified antibody is used, the amount of the antibody is preferably from 0.001 to 5% by weight, more preferably from 0.005 to 1% by weight, calculated as a freeze-dried antibody. If the proportion is less than 0.001% by weight, the effects will be insufficient, whereas proportions in excess of 5% by weight will not achieve increased effects commensurate with the amounts used. Rather, they will lead to a rise in manufacturing costs and are therefore not preferable. In the case where a roughly purified antibody is used, the amount of the antibody is preferably from 0.01 to 50% by weight, more preferably from 0.01 to 20% by weight, calculated as a freeze-dried antibody.

The polymer emulsion (b) which is used in the present invention is a dispersion of very fine polymer particles which are stably held in an aqueous solution of water or an organic solvent by the stabilizing powder of hydrophilic groups possessed by surfactants, protective colloids, or polymers themselves.

Preferably, the polymer emulsion (b) according to the present invention is an emulsion of a polymer which does not contain silicon atoms. Examples of this type of polymer include polymers and copolymers of vinyl monomers; polycondensation resins such as polyamide resins; alkyd resins; polyester resins, etc; poly-addition resins such as polyurethanes; and chemically modified products of high molecular weight materials of natural origin such as cellulose derivatives and natural high molecular weight materials such as natural rubber. They are used singly or in arbitrary combinations of two or more. Among the above polymers, polymers and copolymers of vinyl monomers, alkyd resins, polyurethanes and polyester resins are preferred.

Examples of the vinyl monomers include (meth)acrylic acid, (meth)acrylic acid esters, (meth)acrylic amides, ethylene, propylene, isoprene, butadiene, styrene, and vinyl acetate. Examples of the copolymers of vinyl monomers include copolymers of arbitrary combinations of one or more vinyl monomers listed above.

The polymer emulsion (b) which is used in the present invention can be prepared, for example, by a method in which the polymer is forcibly emulsified in water in the presence of a surfactant; a method in which water is added to a solution of a polymer in a water-miscible organic solvent to precipitate the polymer as fine particles; a method in which a solution of a polymer having salt-forming groups in a water-miscible organic solvent is neutralized, after which the solvent is replaced by water; or by a method in which a hydrophilic/hydrophobic amphipathic polymer is self-emulsified in an aqueous medium.

Examples of commercially available products of the polymer emulsion (b) include Resin 125-221 and Iodosol A-4540 (both products by Kanebo NSC, acrylic ester—vinyl acetate copolymers), Rikabond ES-23 (by Chuo Rika Kogyo, acrylic ester—styrene copolymer), JSR-2108 (by Japan Synthetic Rubber, styrene—butadiene copolymer), JSR-0668 (by Japan Synthetic Rubber, carboxy-modified styrene—butadiene copolymer), AE331 (by Japan Synthetic Rubber, carboxy-modified acrylic resin, average particle size: 0.2 to 0.3 $\mu$m), E-5003 (by Nippon Paint, butyl polyacrylate micro emulsion, average particle size: 60 nm), E-2002 (by Nippon Paint, methyl polyacrylate micro emulsion, average particle size: 30 nm), Adekabontiter-HUX-290H (by Asahidenka Kogyo, polyurethane emulsion, average particle size: 2.0 $\mu$m), Adekabontiter-HUX-240 (by Asahidenka Kogyo, polyurethane emulsion, colloid region), Arolon 580 (by Nippon Shokubai, short chain oily alkyd resin emulsion), etc. Emulsified products obtained from Sanwax E-300 (by Sanyo Kasei, emulsified low-molecular polyethylene) and Nonipol 100 (by Nippon Shokubai, polyoxyethylene nonylphenylether) may also be used.

The size of the fine particles contained in the polymer emulsion is not particularly limited. The average particle size is preferably from 0.001 to 50 $\mu$m, more preferably from 0.01 to 5 $\mu$m, and particularly preferably from 0.01 to 1 $\mu$m. If the average particle size is less than 0.001 $\mu$m, tactile feel upon use is not sufficiently improved, whereas average sizes in excess of 50 μm result in poor tactile feel upon use.

The amount of the emulsion (b) is preferably from 0.001 to 50% by weight, more preferably 0.01 to 10% by weight, and particularly preferably from 0.01 to 5% by weight, as converted to a drying state. If the proportion is less than 0.001% by weight, the effects will be insufficient, whereas proportions in excess of 50% by weight will not achieve increased effects commensurate with the amounts used. Rather, they will lead to a rise in manufacturing costs and are therefore not preferable.

The hair cosmetic compositions of the present invention may further contain, in addition to the above-described essential components, other optional components such as surfactants, cationic polymers, a variety of silicone derivatives, and other known hair cosmetic components.

Examples of the surfactants include anionic surfactants such as alkylbenzene sulfonates, alkyl ether sulfates, olefin sulfonic acid, alpha-sulfofatty esters, amino acid surfactants, phosphoric ester surfactants, sulfosuccinic ester surfactants; amphoteric surfactants such as sulfonic acid surfactants, betaine surfactants, alkylamine oxides, and imidazoline surfactants; nonionic surfactants such as polyoxyethylene alkyl ethers, polyoxyethylene alkyl phenyl ethers, alkanolamides, and their alkylene oxide adducts, esters of polyols and fatty acids, sorbitan fatty acid esters, and alkyl saccharide surfactants; and cationic surfactants such as mono- or di-linear long chain alkyl quaternary ammonium salts and mono- or di-branched long chain alkyl quaternary ammonium salts. These are used singly or in combination of two or more. When the hair care composition to be manufactured is a shampoo, it is preferred that amino acid surfactants, phosphoric ester surfactants, sulfosuccinic ester surfactants, imidazoline surfactants, or alkylsaccharide surfactants be used in appropriate combinations in view of the mildness to the skin and hair. The amount of the surfactants in the hair cosmetic composition is preferably from 0.01 to 40.0% by weight, and preferably from 0.5 to 20.0% by weight.

Examples of the cationic polymers include cationic cellulose derivatives, cationic starches, cationic guar gum derivatives, diallyl quaternary ammonium salt/acrylic amide copolymers, quaternarized polyvinylpyrrolidone derivatives, and polyglycol-polyamine condensation products. These are used singly or in combination of two or more. Specific examples of these cationic polymers include cationic celluloses having a molecular weight of about 100,000 to 3,000,000, cationic starches having a cationization degree of about 0.01 to 1, cationic guar gums having a cationization degree of about 0.01 to 1 (for example, Jaguar produced by Mayhole), diallyl quaternary ammonium salt/ acrylic amide copolymers with a molecular weight of from 30,000 to 2,000,000, quaternarized polyvinylpyrrolidone derivatives such as polyvinylpyrrolidone-dimethylaminoethyl methacrylate copolymers with a molecular weight of from 10,000 to 2,000,000 and with a cationic nitrogen content in the vinyl polymer of from 1.8 to 2.4% by weight, polyglycolpolyamine condensation products having C6–C20 alkyl, adipic acid/ dimethylaminohydroxypropyl diethylene triamine copolymers (for example, Caltaretin by Sandos), and other cationic polymers described in Japanese Patent Application Laid-open (kokai) No. 53-139,734 (see page 14, line 5 of the upper left column to page 37, line 12 of the upper right column) and Japanese Patent Application Laid-open (kokai) No. 60-36,407 (see page 8, line 16 of the upper right column to page 10, line 20 of the lower left column). The amount of the cationic polymers incorporated into the hair cosmetic composition of the invention is preferably from 0.05 to 20.0% by weight, more preferably from 0.1 to 10.0% by weight, and particularly preferably from 0.1 to 5.0% by weight, based on the total weight of the composition.

Examples of the silicone derivatives include dimethylpolysiloxanes, methylphenylpolysiloxanes, amino-modified silicones, alcohol-modified silicones, aliphatic alcohol modified silicones, polyether-modified silicones, epoxy-modified silicones, fluorine-modified silicones, cyclic silicones, and alkyl-modified silicones. They are used singly or in combination of two or more. They may be used in the form of a latex composition which is prepared by an emulsification polymerization described in Japanese Patent Kokoku Publication No. 56-38,609 (page 3, lines 29–43 of column 6). Of these silicone derivatives, preferable ones are dimethylpolysiloxanes, polyether modified silicones, amino-modified silicones, and cyclic silicones with a polymerization degree of not less than 500 in view that they can impart favorable sensation to the hair. The amount of silicone derivatives to be incorporated into the hair cosmetic composition of the invention is preferably from 0.01 to 20.0% by weight, more preferably from 0.05 to 10.0% by weight, and particularly preferably from 0.1 to 5.0% by weight, based on the total weight of the composition.

Examples of other known hair cosmetic components include sensation improvers such as salts of higher fatty acids, alkylamine oxides, fatty acid akanolamides, squalane, lanolin, alpha-monoisostearylglyceryl ether, and cholesteryl sulfates; humectants such as propylene glycol, glycerol, sorbitol, amide derivatives of the following formula (1) disclosed in Japanese Patent Application Laid-open (kokai) No. 64-9,913:

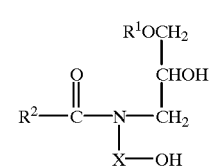

(1)

wherein $R^1$ is a C10–C26 linear or branched, saturated or unsaturated hydrocarbon group, $R^2$ is a C9–C25 linear or branched, saturated or unsaturated hydrocarbon group, and X is a group $(CH_2)_m$, wherein m is an integer from 2 to 6 inclusive, and dialkylene glycol monoalkyl ethers of the following formula (2):

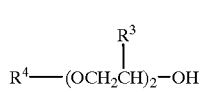

(2)

wherein $R^3$ is hydrogen or methyl, and $R^4$ is C1–C5 alkyl; viscosity modifiers such as methylcellulose, carboxyvinyl polymers, hydroxyethylcellulose, polyoxyethylene glycol distearate, and ethanol; pearl-luster imparting agents; perfumes; colorants; UV absorbers; antioxidants; bactericides such as trichlosan and trichlocarban; antiinflammatory agents such as potassium glycyrrhizate and tocopherol acetate; antidandruff agents such as zinc pyrithione and octopirox, preservatives such as methylparaben and butylparaben; chelating agents such as aminopolycarboxylic acid derivatives including ethylenediaminetetraacetic acid; permeation accelerators such as benzyl alcohol and benzyloxy ethanol.

The pH of the hair cosmetic composition according to the present invention is preferably in the range from 3 to 10, and more preferably from 4 to 8. The hair cosmetic composition of the present invention may take any physical forms, depending on the purpose of use, including aqueous solutions, ethanol solutions, emulsion solutions, emulsions, suspensions, gels, liquid crystals, solids, and aerosols. The hair cosmetic composition of the invention may be prepared into, for example, preshampoos, shampoos, hair rinses, hair conditioners, hair treatments, setting lotions, blow-styling lotions, hair sprays, styling mousses, styling gels, hair liquids, hair tonics, hair creams, 1st liquids for permanent wave treatment, 2nd liquids for permanent wave treatment, permanent hair dyes, and instant hair dyes.

EXAMPLES

The present invention will next be described by way of examples, which should not be construed as limiting the invention.

Preparation Example 1
Preparation of a Hair Antigen
(1) Preparation of Coarse Hair Powder Healthy hair or hair which had undergone a permanent treatment was immersed in an aqueous solution of lithium bromide (11 M). The hair was allowed to swell in a hot bath of 90° C. for 90 minutes. Eventually, the hair was deformed like rubber. Excessive liquid was removed from the thus treated hair by using a nylon net, after which the hair was transferred to a mortar which had been cooled in advance. The hair was frozen with liquid nitrogen, and was crushed for 3 hours while maintaining its frozen state by supplementing liquid nitrogen when it was necessary. The crushed hair was put in a tube for centrifugation, washed with ion-exchange water, and was centrifugally separated to collect the hair. This procedure was repeated two times. Thereafter, lithium bromide was completely washed off from the hair, obtaining crude hair powder (average size: not more than 100 $\mu$m).

(2) Preparation of Fine Hair Powder

The coarse hair powder described above and ion-exchange water were placed in a tube for centrifugation. The tube was vigorously shaken to disperse the hair. Thereafter, the tube was allowed to stand for 1 minute. The supernatant containing fine powder was collected, and the remainder part was subjected to the same treatment repeatedly. The thus collected fine powder was dispersed in distilled water (1% by weight) and was crushed three times with 200 psi. using a French press. Subsequently, the crushed hair powder was freeze-dried to obtain a fine hair powder (average size: not more than 10 $\mu$m).

(3) Preparation of Cuticle Powder

First, hair was chopped to a size of 1 cm or less. After excessive sebum was removed from the chopped hair using hexane, the hair was sterilized with 70% by weight of ethanol. Separately, a Sakaguchi flask containing 100 ml ion-exchange water was sterilized in an autoclave. To the sterilized flask, 20 Teflon balls each having a diameter of about 12 mm and 2 g of the sterilized hair were placed. Thereafter, the flask was shaken at 150 rpm for 2 days to effect a shaking culture. The ion-exchanged water which became turbid due to the presence of separated cuticles was recovered and freeze-dried, obtaining a cuticle powder.

(4) Preparation of Cortex (Including Medulla) Powder

Hair was immersed in an aqueous nickel chloride solution (36 ppm) at 25° C. for 10 seconds. Immediately thereafter, the hair was rinsed with ion-exchange water, and was treated with an aqueous hypochlorous acid (a solution of about 5% by weight of chlorine, adjusted to pH 6.5 with conc. HCl) at 20° C. for 2 minutes, during which cuticles were fractured by oxygen explosion. Immediately thereafter, rinsing was performed using ion-exchange water. Next, the hair was treated with 0.5% by weight of sodium pyrosulfate solution (pH 9.5) at 20° C. for 2 minutes to remove residual chlorine, and the remaining cuticles were rubbed off in warm ion-exchange water. Subsequently, the hair was immersed in 0.1 N acetic acid solution for 1 minute, after which it was rinsed with cold ion-exchange water and dried to obtain a treated hair from which cuticles were removed. The thus obtained hair was freeze-dried in a manner similar to that described in (1) above, obtaining a cortex powder.

(5) Preparation of a Keratin Protein Extracted From Hair

Hair was chopped to a size of 3 mm or less. It was added to Tris HCl buffer (200 mM, pH 9.0) containing 8 M of urea and 200 mM of 2-mercaptoethanol, followed by culturing in an atmosphere of nitrogen at 40° C. for 2 hours. Subsequently, the hair was ground with a Teflon homogenizer, and cultured again at 40° C. for 2 hours. The culture was subjected to a centrifugation at 10,000×G for 30 minutes to collect a supernatant. The supernatant was allowed to react with a solution of acetic iodide at pH 8.0. The reaction was terminated by adding 2-mercaptoethanol. The reaction mixture was dialyzed using ion-exchange water for 2 days, freeze-dried to obtain a sample of keratin protein of hair. The sample was dissolved in Tris HCl buffer containing urea and 2-mercaptoethanol, and dialyzed with Tris HCl buffer (pH 7.4) containing 0.1% by weight of sodium dodecyl sulfate, obtaining a keratin protein of hair.

Preparation Example 2
(1) Preparation of an Antibody From Egg Yolk

Samples of the hair, hair constituent powders, and extracted keratin protein obtained in (1) to (5) of Preparation Example 1 above were respectively dispersed in saline, and each was mixed with a complete Freund adjuvant. Using the resulting mixtures, hens were over-immunized (intramuscular injection (1 mg/ml)×4 times). From eggs produced by the immunized hens, antibodies were obtained by the following method. First, a yolk and an aqueous lambda-carrageenan solution (1.5 ml/ml, 5 times the volume of the yolk) were mixed. Lipoprotein was coagulated, and was removed by centrifugal separation. Thus, 5 supernatant samples were obtained. Each supernatant sample contained a yolk antibody which was recovered at a recovery ratio of about 80%.

(2) Preparation of a Purified Egg Yolk Antibody

Using the 5 different supernatant samples obtained in (1) above and sodium sulfate, fractionation was performed to obtain 5 kinds of purified egg yolk antibody (precipitation from 17% (w/v) sodium sulfate).

Preparation Example 3
(1) Preparation of an Acrylic Resin Emulsion of a Self-Dispersion Type In a reactor equipped with a stirrer, a reflux condenser, a dropping funnel, a thermometer, and a nitrogen introducing tube, the following materials were charged: isopropyl alcohol (500 parts by weight), ethyl acrylate (314 parts by weight), ethyl methacrylate (85 parts by weight), dimethylaminoethyl methacrylate (65 parts by weight) and methacrylic acid (86 parts by weight). Air in the reactor was replaced by a nitrogen gas. Thereafter, 2,2'-azobisisobutyronitrile (0.5 parts by weight) was added thereto. Polymerization was allowed to proceed at 80±2° C. for 7 hours to obtain a copolymer. The copolymer was diluted with isopropyl alcohol (250 parts by weight), and neutralized with 1 N NaOH (150.7 parts by weight). Thereafter, ion-exchange water (2,500 parts by weight) was added. Isopropyl alcohol was distilled off under reduced pressure at a temperature not higher than 50° C. to obtain a self-emulsified emulsion. The average particle size of this emulsion was 0.03 μm.

(2) Preparation of an Emulsion by Emulsion Polymerization

In a reactor of the same type used in (1) above, water (150 parts by weight), sodium dodecylbenzene sulfonate (2 parts by weight), ammonium persulfate (0.5 parts by weight), methyl methacrylate (55 parts by weight), n-butyl acrylate (33 parts by weight), styrene (10 parts by weight), acrylic acid (2 parts by weight), dibutyl phthalate (5 parts by weight), and dodecylmercaptan (2.5 parts by weight) were charged, and the air in the reactor was replaced by a nitrogen gas. Dissolved oxygen was also removed. Thereafter, the content of the reactor was heated to 70° C. with stirring for 3 hours for polymerization. Subsequently, 3 hours of curing was effected at the same temperature. A small amount of coagulated matter was removed to obtain an emulsion (solids contained: 41% by weight). The average particle size of this emulsion was 0.12 μm.

(3) Preparation of a Polyester Emulsion

In a reactor equipped with a stirrer, a condenser, a recipient, a thermometer, and a nitrogen introducing tube, the following materials were charged: dimethyl terephthalate (108 parts by weight), ethylene glycol (37 parts by weight), polyethylene glycol (#4000, 450 parts by weight), and antimony trioxide (0.3 parts by weight). The air in the reactor was replaced by a nitrogen gas. Thereafter, nitrogen was blown to the reactor with stirring, and the temperature was elevated to 240° C. to proceed an esterifying reaction under ambient pressure for 5 hours. The hydroxyl value of the reaction product was 28.0, and the weight-average molecular weight obtained from a gel filtration analysis was 3,900. The reaction product (120 parts by weight) was combined with ion-exchange water (480 parts by weight), and the mixture was emulsified for 2 hours at 60° C. As a result, an emulsion containing 20.5% by weight of solids was obtained. The average particle size of this emulsion was 8 μm.

Example 1

Preparation of Hair Treatments

Hair cosmetic compositions (hair treatments) of the present invention (Nos. 1 to 12) and comparative products (Nos. 13–15) shown in Tables 1 and 2 were prepared. These compositions were evaluated with respect to the softness of the hair, greasiness, moistened sensation, smoothness, and occurrence of split hairs. The results are also shown in Tables 1 and 2.

Test Method

Bundles of hair fibers (hair samples of Japanese women, each weighing 20 g, about 15–20 cm long) were provided, and shampooed with an ordinary shampoo. Each hair treatment composition (2 g) from invention products and comparative products was uniformly applied to the hair sample, after which the hair was rinsed with running water for 30 seconds. When two treatments were carried out in a consecutive manner, the sample which had undergone a first treatment was rinsed with running water, uniformly applied with 2 g of a comparative hair treatment composition, and then rinsed with running water for 20 seconds. The hair samples thus treated were towel-dried and further dried with a dryer. The resulting dried hair samples were evaluated in terms of the following test items using the criteria below.

Softness of the hair:

A: Very soft

B: Soft

C: Moderate

D: Hard

Lack of greasiness:

A: Least greasiness

B: Slight greasiness

C: Moderate

D: Much greasiness

Moistened sensation:

A: Very moistened feel

B: Fairly moistened feel

C: Neither moistened feel or dry feel,

D: Dry and rough feel

Smoothness:

A: Very smooth

B: Smooth

C: Moderate

D: Frictional

Occurrence of split hairs:

A: Very small number of split hairs

B: Small number of split hairs

C: Hard to tell

D: Many split hairs

Test Results

As is apparent from Tables 1 and 2, Invention Products 1 to 12 which contained both components (a) and (b) imparted softness, moistness, and smoothness to the hair with reduced greasiness and reduced occurrence of split hair. By contrast, Comparative Products 13 to 15 which contained either one of components (a) or (b) exhibited poor results in any one of the evaluation items. Furthermore, consecutive treatments using pairs of Comparative Products 13 and 14 or 13 and 15 did not exhibit satisfactory results, either. From these results, it is understood that the effects of the present invention are obtained only when components (a) and (b) are both present in the composition.

TABLE 1

|  | Invention Products | | | | | | | | |
| --- | --- | --- | --- | --- | --- | --- | --- | --- | --- |
|  | 1 | 2 | 3 | 4 | 5 | 6 | 7 | 8 | 9 |
| Stearyl trimethylammonium chloride | 1 | 1 | 1 | 1 | 1 | 1 | 1 | 1 | 1 |
| N-(2-decyl)tetradecyl-N,N,N-trimethylammonium chloride | 1 | 1 | 1 | 1 | 1 | 1 | 1 | 1 | 1 |
| Cetyl alcohol | 2 | 2 | 2 | 2 | 2 | 2 | 2 | 2 | 2 |
| Propylene Glycol | 4 | 4 | 4 | 4 | 4 | 4 | 4 | 4 | 4 |
| Diethyleneglycol monoethylether | 4 | 4 | 4 | 4 | 4 | 4 | 4 | 4 | 4 |

TABLE 1-continued

|  | Invention Products | | | | | | | | |
|---|---|---|---|---|---|---|---|---|---|
|  | 1 | 2 | 3 | 4 | 5 | 6 | 7 | 8 | 9 |
| Purified antibody of Preparation Example 2(2), (antigen = coarse hair powder of Example 1(1)) | 0.001 | 0.001 | 0.001 | 0.001 | 0.001 | 0.001 | 0.001 | 0.001 | 0.001 |
| Emulsion of Preparation Example 3(1) (average particle size: 0.03 μm) | 0.01 | 1 | 2.0 | 0.01 | 1 | 2.0 | — | — | — |
| Emulsion of Preparation Example 3(2) (average particle size: 0.12 μm) | — | — | — | — | — | — | 0.01 | 1 | 2.0 |
| Evaluation Items: | | | | | | | | | |
| Softness | B | B | B | B | B | B | A | B | B |
| Lack of greasiness | A | A | A | A | A | A | A | A | A |
| Moistened feel | A | A | A | A | A | A | A | A | A |
| Smoothness | B | A | B | A | B | B | B | A | A |
| Occurrence of split hairs | B | B | A | B | A | A | B | B | A |

TABLE 2

|  | Invention Products | | | | | | Comparative Products | |
|---|---|---|---|---|---|---|---|---|
|  | 10 | 11 | 12 | 13 | 14 | 15 | 13–14 | 13–15 |
| Stearyl trimethylammonium chloride | 1 | 1 | 1 | 1 | 1 | 1 | | |
| N-(2-decyl)tetradecyl-N,N,N-trimethylammonium chloride | 1 | 1 | 1 | 1 | 1 | 1 | | |
| Cetyl alcohol | 2 | 2 | 2 | 2 | 2 | 2 | | |
| Propylene Glycol | 4 | 4 | 4 | 4 | 4 | 4 | | |
| Diethyleneglycol monoethylether | 4 | 4 | 4 | 4 | 4 | 4 | | |
| Purified antibody of Preparation Example 2(2), (antigen = course hair powder of Example 1(1)) | 0.01 | 0.01 | 0.01 | 0.01 | — | — | | |
| Emulsion of Preparation Example 3(1) (average particle size: 0.03 μm) | — | — | — | — | 0.01 | — | | |
| Emulsion of Preparation Example 3(2) (average particle size: 0.12 μm) | 0.01 | 1 | 2.0 | — | — | 0.01 | | |
| Evaluation Items: | | | | | | | | |
| Softness | A | A | B | B | C | C | B | B |
| Lack of greasiness | A | A | A | A | D | D | A | A |
| Moistened feel | A | A | A | B | C | C | B | B |
| Smoothness | A | A | A | B | C | C | B | B |
| Occurrence of split hairs | B | A | A | B | C | C | B | B |

Example 2

Shampoos

Hair cosmetic compositions (shampoos) of the present invention (Invention Products 16 to 21) and comparative products (Comparative Products 20 and 21) shown in Table 3 were prepared. These compositions were evaluated with respect to the softness of the hair, greasiness, moistened sensation, smoothness, and occurrence of split hairs in accordance with the methods described in Example 1. The results are also shown in Table 3. As is apparent from the Table, overall excellent results were obtained only when Invention Products were used, i.e., both components (a) and (b) were present in the shampoo compositions.

TABLE 3

|  | Invention products | | | | Comparative products | | |
|---|---|---|---|---|---|---|---|
|  | 16 | 17 | 18 | 19 | 20 | 21 | 20–21 |
| Sodium polyoxyethylene(2.5) lauryl sulfate | 20 | 20 | 20 | 20 | 20 | 20 | |
| N-lauroyl-N'-carboxymethyl-N'-(2-hydroxyethyl)ethylenediamine-triethanolamine salt | 3 | 3 | 3 | 3 | 3 | 3 | |
| Coconut oil fatty acid diethanolamide | 1 | 1 | 1 | 1 | 1 | 1 | |
| Yolk protein of Preparation Example 2(1), (antigen = fine hair powder of Example 1(2)) | 0.1 | — | — | — | 0.1 | — | |
| Yolk protein of Preparation Example 2(1), (antigen = cuticle powder of Example 1(3)) | — | 0.1 | — | — | — | — | |
| Yolk protein of Preparation Example 2(1), (antigen = fine cortex powder of Example 1(4)) | — | — | 0.1 | — | — | — | |
| Yolk protein of Preparation Example 2(1), (antigen = extracted keratin protein of Example 1(2)) | — | — | — | 0.1 | — | — | |

TABLE 3-continued

|  | Invention products | | | | Comparative products | | |
| --- | --- | --- | --- | --- | --- | --- | --- |
|  | 16 | 17 | 18 | 19 | 20 | 21 | 20–21 |
| Polyester Emulsion of Preparation Example 3(3) (average particle size: 8 μm) | 0.01 | 0.01 | 0.01 | 0.01 | — | 0.01 | |
| Evaluation Items: | | | | | | | |
| Softness | A | A | A | A | B | D | B |
| Lack of greasiness | A | A | A | A | A | D | A |
| Moistened feel | A | A | A | A | B | C | B |
| Smoothness | A | A | A | A | B | B | A |
| Occurrence of split hairs | A | A | A | A | A | C | A |

Example 3

In order to substantiate the fact that the yolk antibody to hair functions to have particles in the polymer emulsion specifically (or selectively) adsorbed onto the damaged part of the hair fibers, hair was treated with a polystyrene latex containing a fluorescent dye and observed under a fluorescent microscope. Polystyrene latex containing a fluorescent dye (product of Polyscience, average particle size: 3 μm) was added to an aqueous solution containing 0.01% by weight of the yolk antibody prepared according to Preparation Example 2(1) and mixed to obtain 0.05% by weight of a polystyrene mixture. The mixture was cultured at room temperature for 30 minutes, after which damaged hair due to a permanent treatment was immersed therein. Culturing was continued for further 30 minutes. Thereafter, the hair was thoroughly washed with water, dried, and observed under a fluorescent microscope for the adsorption of polystyrene latex on the hair fibers. For comparison, the same treatment was repeated using damaged hair and a purified yolk antibody prepared according to Preparation Example 2 from an egg produced by a hen which had not been immunized with hair powder.

As a result, it was found that when the hair was treated with a composition containing the anti-hair yolk antibody and polystyrene latex, the polystyrene latex particles were primarily adsorbed onto the damaged sites of the hair fibers where cortex was exposed, whereas in the case where the comparative yolk antibody was used, only a very small amount of polystyrene latex particles was adsorbed. Therefore, it is concluded that the anti-hair yolk antibody makes polystyrene latex particles to be adsorbed specifically and selectively onto the damaged part of hair fibers.

Example 4

A hair rinse composition of the following formula was prepared by a routine method.

| Formula | (wt. %) |
| --- | --- |
| Di(2-hexadecyl)dimethylammonium chloride | 2.0 |
| Cetyltrimethylammonium chloride | 2.0 |
| (Myristoylaminoethyl-N-hydroxyethyl)amino-2-hydroxypropyltrimethylammonium | 1.0 |
| Cetyl alcohol | 5.0 |
| Polyoxyethylene(E.O.5)oleyl ether | 0.4 |
| Dimethylpolysiloxane (polymerization degree: 1000) | 0.5 |
| Pentaerithritol glyceryl.isostearylglycidyl ether, 1 mol adduct | 0.1 |

-continued

| Formula | (wt. %) |
| --- | --- |
| Antibody of Preparation Example 2(1), (antigen = coarse hair powder of Preparation Example 1(1)) | 0.2 |
| E-5003 (butyl acrylate micro emulsion, average particle size: 60 nm) | 0.5 |
| Liquid paraffin | 1.0 |
| Hydroxyethylcellulose (1% aqueous solution, viscosity: 8000 cP) | 0.3 |
| Methylparaben | 0.2 |
| Perfume | 0.2 |
| Purified water | balance |
| Total | 100 |

This hair rinse provided excellent smoothness and softness, and reduced greasiness. It also provided a favorable moistened tactile feel to the hair.

Example 5

A hair treatment composition of the following formula was prepared by a routine method.

| Formula | (wt. %) |
| --- | --- |
| Di(2-hexadecyl)dimethylammonium chloride | 2.0 |
| Cetyltrimethylammonium chloride | 2.0 |
| Cetyl alcohol | 5.0 |
| (Myristoylaminoethyl-N-hydroxyethyl)amino-2-hydroxypropyltrimethylammonium | 1.0 |
| Antibody of Preparation Example 2(1), (antigen = coarse hair powder of Preparation Example 1(1)) | 0.7 |
| Adekabontiter-HUX-290H (polyurethane emulsion; average particle size: 2.0 μm) | 0.5 |
| Polyoxyethylene(E.O.5)oleyl ether | 0.4 |
| Hydroxyethylcellulose (1% aqueous solution, viscosity: 8000 cP) | 0.3 |
| Methylparaben | 0.2 |
| Perfume | 0.2 |
| Purified water | balance |
| Total | 100 |

This hair treatment provided excellent smoothness and softness, and reduced greasiness. It also provided a favorable moistened tactile feel to the hair.

Example 6

A shampoo composition of the following formula was prepared by a routine method.

| Formula | (wt. %) |
|---|---|
| Sodium polyoxyethylene(E.O.2.5)lauryl ether sulfate | 15.0 |
| Coconut oil fatty acid diethanolamide | 3.0 |
| Antibody of Preparation Example 2(2), (antigen = keratin protein extracted from the hair in Preparation Example 1(5)) | 0.5 |
| AE331 (carboxy-modified acrylic emulsion, average particle size: 0.2–0.3 $\mu$m) | 0.1 |
| SM8702C (amino-modified silicone, product of Toray silicone) | 0.5 |
| Propylene glycol | 10.0 |
| Perfume | 0.2 |
| Colorant | trace |
| NaOH (pH modifier) | suitable amount |
| Purified water | balance |
| Total | 100 |

This shampoo composition provided excellent smoothness and softness, and reduced greasiness. It also provided a favorable moistened tactile feel to the hair.

Since the hair cosmetic composition according to the present invention contains an antibody (a) prepared using hair or a hair extract as an antigen, a conditioning component of the composition, polymer emulsion (b), can be adsorbed onto the hair very effectively. If the antibody (a) is prepared using damaged hair as an antigen, polymer emulsion (b) is selectively adsorbed onto only the damaged part of the hair. Therefore, when hair is treated with the present hair cosmetic composition, softness, moistness, and smoothness can be imparted to the hair in the dry state with reduced greasiness. At the same time, the composition of the invention can prevent occurrence of split hairs and also repair the split hairs. These effects are not lost by repeated ordinary shampooings.

What is claimed is:

1. A hair cosmetic composition which comprises (a) an antibody to hair or to a hair extract, said antibody obtained from egg yolk of poultry immunized with the hair or hair extract and (b) latex particles of a polymer or copolymer of a vinyl monomer selected from the group consisting of (meth)acrylic amide, ethylene styrene, propylene, butadiene, isoprene and mixtures thereof.

2. The hair cosmetic composition according to claim 1, wherein the antigen which is used for immunization is selected from the group consisting of crushed whole hair, crushed cuticles, crushed cortex, hair keratin and a hydrolysate of hair keratin.

3. The hair cosmetic composition according to claim 1, further comprising a surfactant (c).

4. The hair cosmetic composition according to claim 1, further comprising a silicone compound (d).

5. The hair cosmetic composition according to claim 1, further comprising a cationic polymer (e).

6. The hair cosmetic composition according to claim 1, wherein the antibody (a) is contained in a proportion of from 0.001 to 50% by weight, and the latex particles (b) are incorporated in a proportion of from 0.001 to 50% by weight in terms of a dry state.

7. The hair treatment composition according to claim 1, which is in a form selected from the group consisting of preshampoos, shampoos, hair rinses, hair conditioners, hair treatments, setting lotions, blow-styling lotions, hair sprays, styling mousses, styling gels, hair liquids, hair tonics, hair creams, 1st liquids for permanent wave treatment, 2nd liquids for permanent wave treatment, permanent hair dyes and instant hair dyes.

8. The hair cosmetic composition as claimed in claim 2, wherein the antigen is crushed whole hair.

9. The hair cosmetic composition as claimed in claim 1, wherein said particles have a particle size of from 0.01 to 1 $\mu$m.

10. The hair cosmetic composition as claimed in claim 8, wherein said particles have a particle size of from 0.01 to 1 $\mu$m.

11. The hair cosmetic composition as claimed in claim 2, wherein the antigen is crushed cortex.

12. The hair cosmetic composition as claimed in claim 11, wherein said particles have a particle size of from 0.01 to 1 $\mu$m.

13. The hair cosmetic composition as claimed in claim 1, wherein said particles are polystyrene latex particles.

14. The hair cosmetic composition as claimed in claim 8, wherein the particles are polystyrene latex particles.

15. A method of adsorbing particles of a polymer emulsion to the damaged portion of hair fibers comprising contacting damaged hair with a cosmetic composition comprising:

(a) an antibody to hair or to a hair extract, said antibody obtained from egg yolk of poultry immunized with the hair or hair extract; and (b) latex particles of a polymer or copolymer of a vinyl monomer selected from the group consisting of (meth)acrylic amide, ethylene styrene, propylene, butadiene, isoprene and mixtures thereof.

* * * * *